United States Patent [19]

Lawrence et al.

[11] Patent Number: 4,732,046

[45] Date of Patent: Mar. 22, 1988

[54] METHOD AND APPARATUS FOR THE INTRODUCTION OF A VAPORIZABLE SAMPLE INTO AN ANALYTICAL TEST APPARATUS

[75] Inventors: André H. Lawrence, Gloucester; Lorne Elias, Nepean, both of Canada

[73] Assignee: Canadian Patents and Development Limited, Ottawa, Canada

[21] Appl. No.: 25,060

[22] Filed: Mar. 12, 1987

Related U.S. Application Data

[63] Continuation-in-part of Ser. No. 824,248, Jan. 30, 1986, abandoned.

[30] Foreign Application Priority Data

Feb. 8, 1985 [CA] Canada .................................. 473884

[51] Int. Cl.[4] .............................................. G01N 35/06

[52] U.S. Cl. ............................... 73/864.21; 73/863.12

[58] Field of Search ........... 73/863.12, 863.11, 863.21, 73/863.23, 864, 864.23, 864.01, 864.21, 864.81, 864.85, 864.86, 864.87, 864.24; 250/287, 282

[56] References Cited

U.S. PATENT DOCUMENTS

| | | | |
|---|---|---|---|
| 3,733,908 | 5/1973 | Linenberg | 73/863.12 |
| 3,918,913 | 11/1975 | Stevenson et al. | 73/864.24 |
| 4,003,257 | 1/1977 | Fletcher et al. | 73/23.1 |
| 4,046,014 | 9/1977 | Boehringer et al. | 73/863.12 |
| 4,128,008 | 12/1978 | Linenberg | 73/863.12 |
| 4,237,733 | 12/1980 | Kolb et al. | 73/864.23 |
| 4,378,499 | 3/1983 | Spangler et al. | 250/287 |
| 4,476,734 | 10/1984 | Banks et al. | 73/864.85 |
| 4,527,438 | 7/1985 | Fosslien | 73/864.24 |
| 4,551,624 | 11/1985 | Spangler et al. | 250/287 |
| 4,584,887 | 4/1986 | Galen | 73/863.12 |

*Primary Examiner*—Stewart J. Levy
*Assistant Examiner*—Robert R. Raevis
*Attorney, Agent, or Firm*—Ronald G. Bitner

[57] ABSTRACT

This invention is concerned with an apparatus and a method for the introduction of vaporizable samples into an apparatus for the analysis of such samples, such as a gas chromatograph, and especially a capillary gas chromatograph and ion mobility spectrometer. A sample is vaporized or desorbed from a sample tube by heating the sample tube and then transferred by a carrier gas to the analytical apparatus by being withdrawn from the sample tube along and condensed on the inner surface of a heat conductive metal walled needle of a hypodermic syringe from which it is then vaporized and introduced into the analytical apparatus. Suitable samples may also be introduced into an ion mobility spectrometer directly by placing a sample-charged sample tube into a sample-introduction port thereto.

5 Claims, 2 Drawing Figures

8
9
10
11
12
7
6
1
3
2
4
5

METHOD AND APPARATUS FOR THE INTRODUCTION OF A VAPORIZABLE SAMPLE INTO AN ANALYTICAL TEST APPARATUS

This is a continuation-in-part of U.S. patent application Ser. No. 824,248, filed Jan. 30, 1986, now abandoned.

BACKGROUND OF THE INVENTION

Methods for introducing samples into an apparatus for the analysis of vapors and vapor-entrained materials, such as gas chromatographs and ion mobility spectrometers, have hitherto been (1) mainly limited to handling liquids, for example, a syringe carrying a liquid sample is introduced into many conventional gas chromatographs through a rubber septum, or (2) of the type that allows vapor-entrained samples to be introduced from sample tubes. However, the sample introduction means used in these methods must be designed specifically for the particular purpose of analysis. An example of this type of means is the Perkin Elmer Model ATD 50 TM system, two-stage adsorber type gas chromatograph in which a sample is adsorbed onto an adsorbent material such as para-polyphenylene-oxide in the form of TENAX TM contained in a sample tube and then the sample is transferred to an adsorbent material in a second sample tube of different (usually smaller) dimensions from those of the first sample tube. A particular variant of this procedure is described by F. Raschdorf in Chimia 32, 1978. Raschdorf employs a needle method for the introduction of compounds into gas chromatographs. A 100 ml gas syringe is described by Raschdorf and is employed to draw a known volume of sample gas through a thick needle containing an adsorbent such as TENAX. This needle, which functions as a sample tube, is disconnected from the barrel of the syringe and then connected to a supply of carrier gas before being introduced into the gas chromatograph. While the needle of Raschdorf is useful, there are drawbacks in that (a) it requires a large barrelled syringe and adsorbent loaded needle as opposed to the more convenient and conventional sample tubes, (b) a carrier gas entrained sample flow rate of 14 cc/min, which is required to transfer the sample from the syringe to the gas chromatograph, is an order of magnitude too great to be handled by capillary chromatography columns of the type preferred for microanalysis, and (c) hardware modifications may be necessary in the sample introduction port of the chromatograph to accommodate the large needle that is used.

There is a need for a method and an apparatus for the introduction of a vaporizable sample into an analytical test apparatus which uses sample tubes of the conventional type, with the attendant advantages of choice of adsorption material that they allow, but which is also capable of matching the ideal flow for proper desorption through conventional sample tubes of about 30 cc/min., with the optimum flow for capillary gas chromatograph operations of 1–5 cc/min.

SUMMARY OF THE INVENTION

According to the present invention there is provided an apparatus for the introduction of a vaporizable sample into an analytical test apparatus, comprising:

a sample tube having an interior for the collection of a vaporizable sample and from which, when heated, the sample may be vaporized, means at an upstream end of the sample tube for passing a carrier gas to the sample tube interior for elution therefrom of the sample in vapor form;

a hypodermic syringe having a heat dissipating metal walled, hollow needle for the condensation of eluted sample, from the sample tube on an inner surface of the needle, and transfer of sample from the inner surface in a revaporized, concentrated form to the analytical test apparatus;

a valve attached to the hypodermic syringe, at a position adjacent the needle, for venting carrier gas therefrom from which vaporized sample has been condensed in the needle; and a plug closing the downstream end of the sample tube and, in operation, sealing said needle in a perforation for the transfer of the eluted sample from the sample tube to the hypodermic syringe. The apparatus may include heating means for heating the sample tube.

The sample tube may contain sample adsorbent material, such as, for example, a polymeric sample-adsorbent material based on the monomer 2,6-diphenyl-p-phenylene oxide e.g. TENAX-GC TM or material such as platinum gauze, for the entrapment of sample vapors.

The syringe may comprise a barrel and a plunger. The valve for venting the hypodermic syringe may be in the side of the barrel thereof and comprise a pipe containing a closable valve.

The apparatus according to the present invention may be used in combination with cooling means for cooling at least a part of the metal walled, hollow needle. The apparatus according to the present invention may also be used in combination with a carousel for introducing and removing successive sample tubes for the withdrawal of a sample therefrom into the hollow needle with automatic means for the introduction of the hollow metallic needle into the analytical test apparatus.

Further according to the present invention there is provided a method for the introduction of a vaporized sample into an analytical test apparatus, comprising:

(a) collecting said sample in a condensed form in a sample tube;

(b) closing a downstream end of the sample tube with a plug;

(c) inserting a heat dissipating metal walled needle of a hypodermic syringe through the plug;

(d) heating said sample in the tube to render the sample in vapor form;

(e) feeding a carrier gas through the tube to entrain vaporized sample and transport it into the needle;

(f) condensing the sample from the carrier gas onto the inner surface of the needle;

(g) venting carrier gas from which the sample has been condensed, from the hypodermic syringe at a position adjacent the needle, whereby (h) said needle may be introduced into a heated sample intake port of the analytical apparatus, for injection of the sample in a revaporized, concentrated form therein for analysis.

The method according to the present invention may be used with a capillary gas chromatograph or an ion mobility spectrometer.

BRIEF DESCRIPTION OF THE DRAWINGS

In the accompanying drawings which illustrate, by way of example, an embodiment of the present invention.

DETAILED DESCRIPTION OF THE INVENTION

Figure 1:
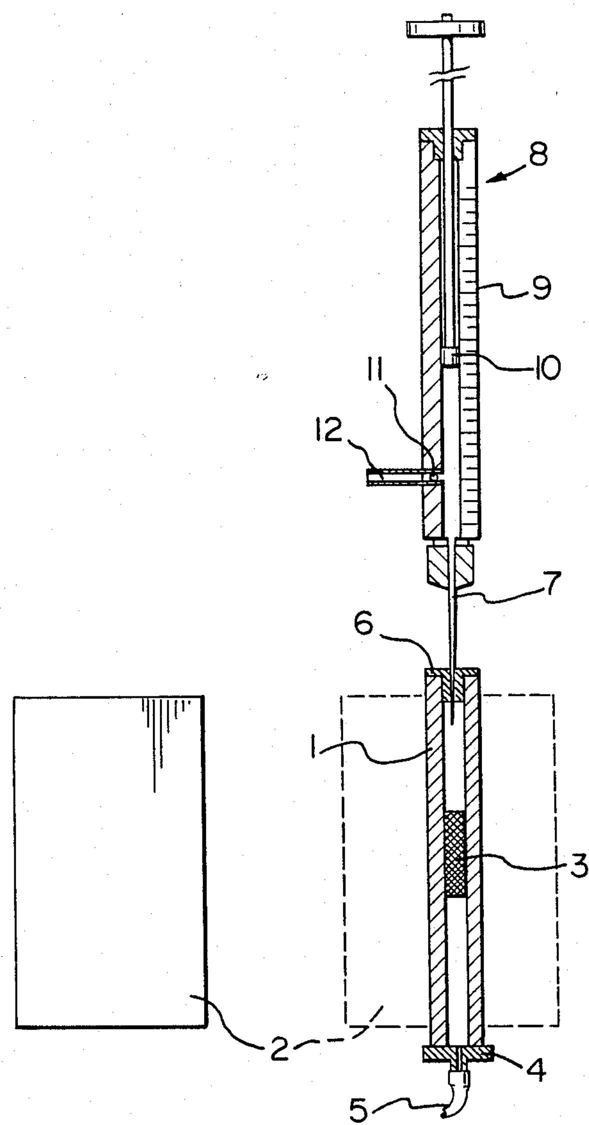
FIGS. 1 and 2 are partly sectional side views of an apparatus for the introduction of a vaporizable sample into an analytical test apparatus.

In FIG. 1, there is shown a sample tube 1 containing platinum gauze 3, which may be placed in heater 2, and connected at an upstream end via a TEFLON TM type polytetrafluorethylene pressure plate 4 to a source of carrier gas 5. At the downstream end of sample tube 1 there is shown a TEFLON plug 6 perforated in sealing engagement by a heat dissipating metal walled, hollow needle 7, said needle 7 forming part of a hypodermic syringe 8 with barrel 9 and plunger 10. A one-way valve 11, connected to a vent 12, is set in the side of barrel 9.

Figure 2:
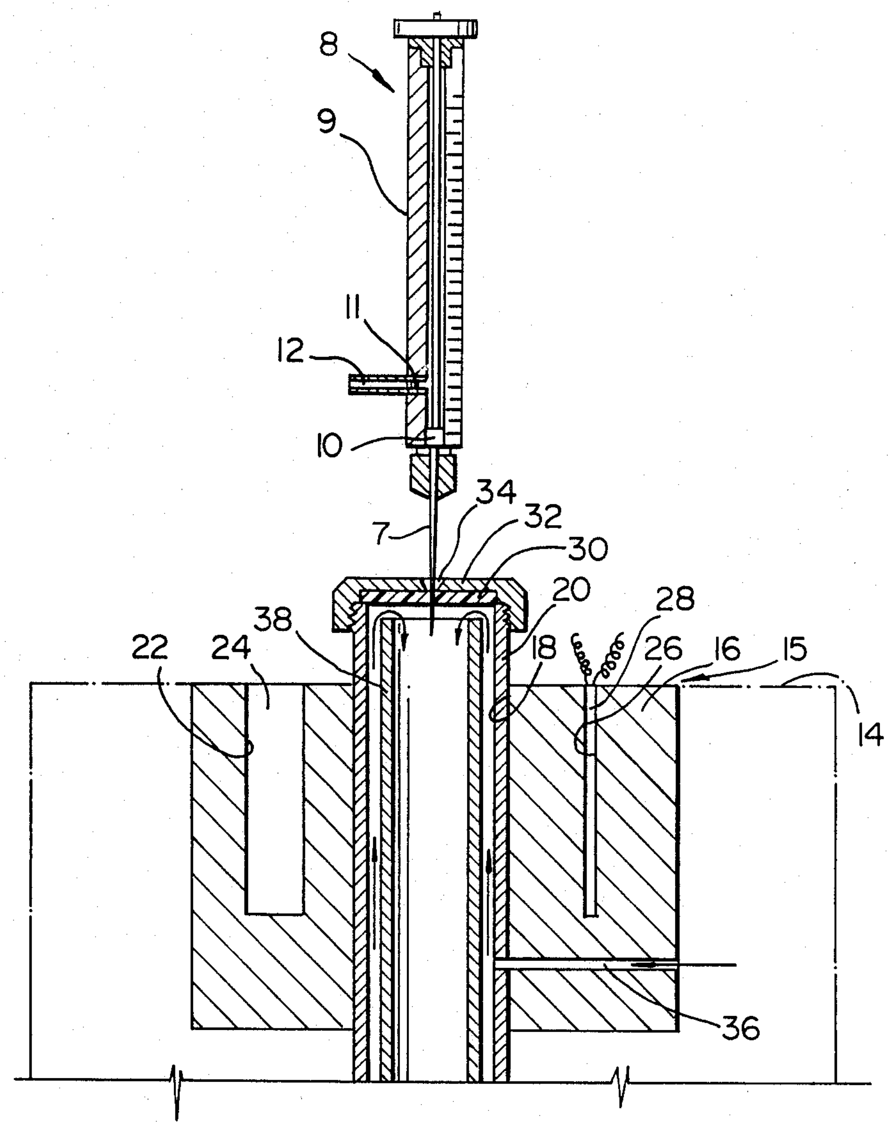

In FIG. 2, similar parts to those shown in FIG. 1 are designated by the same reference numerals and the previous description is relied upon to describe them.

In FIG. 2, there is shown chain dotted the outline of a capillary gas chromatograph 14 having a heated injector port generally designated 15. The heated injector port has a heat conductive metal block 16 provided with a passageway 18 lined with a tubular lining 20, a recess 22 containing a heater 24, and a recess 26 containing a thermocouple 28.

The lining 20 protrudes from the block 16 and has a polytetrafluoroethylene septum 30 and a screw threaded cap 32 sealing the end thereof. The cap 32 has an inwardly tapering needle entry port 34.

The block 16 and the lining 20 have a carrier gas inlet 36.

A partition tube 38 extends along the lining 20 and is spaced from the septum 30.

This embodiment is preferably operated as follows. Sample tube 1 is exposed to a source (not shown) of vaporized sample which is deposited in a condensed form upon the platinum gauze 3. The sample tube 1 is then connected to a source of carrier gas (not shown) by means of a pipe 5 and a TEFLON pressure plate 4. A TEFLON plug 6 is then inserted in the other end of sample tube 1 in a vapor tight manner, the needle 7 is inserted in the plug 6 as illustrated in FIG. 1, and then the one way valve 11 is opened. The heater 2, which may be an aluminum heating block, is then used to heat the sample tube 1 and vaporize the sample. A valve (not shown) controlling the supply of carrier gas to pipe 5 is opened so that the carrier gas and vaporized sample are carried into the needle 7 at a flow rate which is preferably about 30 cc/min, where the sample is condensed and collected on the inner surface of the needle, while the carrier gas is vented through the one-way valve 11 to the vent 12. With the one-way valve of the syringe 8 closed, the needle containing the condensed sample is withdrawn from plug 6 and as shown in FIG. 2 is introduced into the heated injector port 15 of the gas chromatograph 14 by piercing the septum with the needle 7. Carrier gas is passed along the passage 36, along the outside of the partition tube 38 towards the septum 30 where, as shown by the arrows, it enters the partition tube 38 into the separation column (not shown) of the gas chromatograph 14. The condensed sample in the needle 7 vaporizes rapidly on the introduction of needle 7 into the heated injector port 15 of the analytical apparatus. The plunger 10 is then depressed as shown in FIG. 2 to drive the sample vapors from the needle 7 into the carrier gas stream to be entrained therein and conveyed to the separation column of the gas chromatograph 14, typically flowing at a rate of 1–5 cc/min.

If desired, a carousel of the sample tubes may be used, each capped with a TEFLON or rubber plug 6, and provision made for a stream of carrier gas to transfer vaporized samples from successive tubes 1 to the needle 7 of the hypodermic syringe 8. The syringe 8 may be activated by a servo-mechanism to inject successive samples into the heated injector port of the analytical apparatus.

Desirable features of the present invention are (a) conventional sample tubes may be used; (b) laminar flow rate during ejection of the vaporized sample from the needle allows the apparatus to be used with capillary gas chromatographs; (c) the needle may be significantly smaller than needles of the type employed in known apparatus; (d) the needle does not require an adsorbent packing which is used in known apparatus; and (e) no modifications to the analytical apparatus (e.g. gas chromatograph, ion mobility spectrometer) are necessary.

Mixtures of chlorinated biphenyls have been extracted from an air stream into a sample tube of the type shown in FIG. 1. The samples were then transferred to syringe needles and these used to transfer the samples into suitable analytical test apparatus such as a capillary gas chromatograph or ion mobility spectrometer, in the manner described with reference to FIGS. 1 and 2.

Using the apparatus of the type described with reference to FIGS. 1 and 2, very satisfactory chromatographic results have been obtained. The apparatus can yield excellent peak sharpness and reproducibility. Given below are some results for six compounds tested using the apparatus shown in FIGS. 1 and 2.

EXAMPLE 1

| Compound | Amount of Sample Collected On Needle | Heating Time (applied to adsorber) | Heating Temperature | Gas Flow Through Adsorber | Gas Chromatograph Conditions For Analysis | Type of G.C. Detector | Comments |
|---|---|---|---|---|---|---|---|
| Diphenylamine | 2 nanograms ($19^{-9}$ g) | 2 min | 250° C. | Helium 20 psi 15 cc/min | Column is DB-1fused silica, 15 m long, 0.32 mm I.D. Injector Temp. 250° C. Oven Temp. $T_o$ = 60° C. Hold Time: 30 sec. Ramp Rate: (60° C. to 130° C. at 6° C./Min) | nitrogen phosphorous detector (NPD) | needle kept at room temp. |

EXAMPLE 2

| Compound | Amount of Sample Collected On Needle | Heating Time (applied to adsorber) | Heating Temperature | Gas Flow Through Adsorber | Gas Chromatograph Conditions For Analysis | Type of G.C. Detector | Comments |
|---|---|---|---|---|---|---|---|
| 2-methyl-aniline | 10 nanograms ($10^{-9}$ g) | 1½ min | 250° C. | Helium 20 psi 15 cc/min | As example 1 except for: Oven temp. $T_o$ = 60° C. Hold Time: 30 sec. Ramp Rate: 60° C. 130° C. at 6° C. | nitrogen phosphorous detector | needle kept at 0° C. to improve condensation |

EXAMPLE 3

| Compound | Amount of Sample Collected On Needle | Heating Time (applied to adsorber) | Heating Temperature | Gas Flow Through Adsorber | Gas Chromatograph Conditions For Analysis | Type of G.C. Detector | Comments |
|---|---|---|---|---|---|---|---|
| cocaine | 10 nanograms ($10^{-9}$ g) | 2½ min | 250° C. | Nitrogen 20 psi 20 cc/min | As example 1 except for: Oven temp. $T_o$ = 60° C. Hold Time: 1 min Ramp Rate: 60° C. to 150° C. at 20° C./min 150° C. to 200° C. at 6° C./min. | nitrogen phosphorous detector | needle kept at room temperature |

EXAMPLE 4

| Compound | Amount of Sample Collected On Needle | Heating Time (applied to adsorber) | Heating Temperature | Gas Flow Through Adsorber | Gas Chromatograph Conditions For Analysis | Type of G.C. Detector | Comments |
|---|---|---|---|---|---|---|---|
| silvex [ TM ] methylester | 50 picograms ($10^{-12}$ g) | 45 sec | 250° C. | Nitrogen 20 psi 25 cc/min | Column is SE-S4 capillary fused silica 15 mm long × 0.25 mm I.D. Injector Temp. 225° C. Detector Temp. 350° C. Oven Temp. $T_o$ = 100° C. Hold Time = 1 min Ramp rate: 100° C. to 150° C. at 20° C. to 150° C. to 200° C. at 5° C./min | Electron Capture Detector (ECD) | needle kept at room temperature |

EXAMPLE 5

| Compound | Amount of Sample Collected On Needle | Heating Time (applied to adsorber) | Heating Temperature | Gas Flow Through Adsorber | Gas Chromatograph Conditions For Analysis | Type of G.C. Detector | Comments |
|---|---|---|---|---|---|---|---|
| Aldrin [ TM ] | 200 picograms ($10^{-12}$ g) | 45 sec | 250° C. | Nitrogen 10 psi 20 cc/min | As example 4 | Electron Capture Detector (ECD) | needle kept at room temperature |

EXAMPLE 6

Analysis of Heroin using an ion mobility spectrometer

| Compound | Operating Conditions Carrier gas flow rate | Drift gas | Drift tube and injection port temperature | Pressure | Electric field gradient | Gate Width | Drift Length |
|---|---|---|---|---|---|---|---|
| Heroin | 400 cc/min | 660 cc/min | 220° C. | 752 Torr | 214 V/cm | 0.2 msec | 8 cm |

Signal averaging using Nicolet model 535-1-04 [ TM ] signal averager
Heroin gave two ion peaks with drift times of 17.9 and 19.6 msec.
Reduced mobility values of the two peaks ($K_o$) are 1.14 amd 1.04 $cm^2$ $volt^{-1}$ $sec^{-1}$ respectively.

It should be noted that the carrier gas flow through the sample tube 1, when transferring the sample from a sample tube 1 to the needle 7, was found to be of the order of 15–25 cc/min while the gas flow for conveying the vaporized sample from the needle 7 to the gas chromatograph was found to be of the order of 1–1.5 cc/min. From this it will be seen that condensing the vaporized sample in the needle and exhausting carrier gas from the syringe has the effect of delivering a much higher concentration of the sample in the carrier gas that is delivered to the gas chromatograph. For low boiling point compounds such as 2-dimethylaniline (Example 2) the needle should preferably be cooled to below ambient temperatures to improve condensation of the condensed sample in the needle 7. The apparatus according to the present invention has proved particularly useful in the analysis of polychlorinated biphenyls.

In some embodiments of the present invention the inner surface of the needle may comprise a sorbent material for the sample, such as, for example, a silicone coating applied directly to the inner surface of the metal wall, or to a glass capillary lining for the metal wall.

What is claimed is:

1. An apparatus for the introduction of a vaporizable sample into an analytical test apparatus, comprising:
   - a sample tube having an interior for the collection of the vaporizable sample and from which, when the sample tube is heated, the sample may be vaporized and eluted therefrom;
   - means at an upstream end of the sample tube for passing a carrier gas to the sample tube interior;
   - a hypodermic syringe having a heat dissipating metal walled, hollow needle for the condensation of the vaporized, eluted sample, from the sample tube on an inner surface of the needle, and transfer of the sample from the inner surface in a revaporized, concentrated form to the analytical test apparatus;
   - a valve attached to the hypodermic syringe, at a location adjacent the needle, for venting carrier gas therefrom from which vaporized sample has been condensed in the needle; and
   - a plug closing the downstream end of the sample tube and, in operation, sealing said needle in a perforation in said plug for the transfer of the eluted sample from the sample tube to the hypodermic syringe.

2. An apparatus according to claim 1, further comprising heating means for vaporizing the sample in the sample tube for elution therefrom.

3. An apparatus according to claim 1, further comprising sample adsorbent material in the sample tube.

4. An apparatus according to claim 1, wherein the hypodermic syringe further comprises a barrel and a plunger.

5. A method for the introduction of a vaporizable sample into an analytical test apparatus, comprising:
   - (a) collecting said sample in a condensed form in a sample tube;
   - (b) closing the sample tube with a plug;
   - (c) inserting a heat dissipating metal walled needle of a hypodermic syringe through the plug;
   - (d) heating said sample in the tube to render the sample in vapor form;
   - (e) feeding a carrier gas through the tube to entrain vaporized sample and transport it into the needle;
   - (f) condensing the sample from the carrier gas onto the inner surface of the needle;
   - (g) venting carrier gas from which sample has been condensed, from the hypodermic syringe at a position adjacent the needle, whereby
   - (h) said needle may be introduced into a heated sample intake port of the analytical test apparatus, for injection of the sample in a revaporized, concentrated form therein for analysis.

* * * * *